United States Patent [19]

Bradner

[11] 3,988,437

[45] Oct. 26, 1976

[54] SUNTAN COMPOSITION CONTAINING FLUORESCENT COMPOUNDS

[75] Inventor: Hugh Bradner, La Jolla, Calif.

[73] Assignee: Research Corporation, New York, N.Y.

[22] Filed: Mar. 25, 1974

[21] Appl. No.: 454,558

[52] U.S. Cl. .................................... 424/59; 424/22; 424/32; 424/37; 424/47; 424/174; 424/357; 424/360; 252/301.16
[51] Int. Cl.² .......................................... A61K 7/42
[58] Field of Search ................. 424/59; 252/301.2 R

[56] References Cited
UNITED STATES PATENTS

| | | | |
|---|---|---|---|
| 2,104,492 | 1/1938 | Merkel et al. | 424/59 |
| 2,129,131 | 9/1938 | Hunter | 252/301.2 |
| 3,065,238 | 11/1962 | Weidinger et al. | 252/301.2 R |
| 3,177,208 | 4/1965 | Stilz et al. | 252/301.2 R |
| 3,561,990 | 2/1971 | Dressler | 252/301.2 R |

OTHER PUBLICATIONS

Abstract of Application of DeMent, Serial No. 79,113 Published Oct. 28, 1952.
Horrocks, Chem. Abs., 1969, vol. 70, p. 745.
Ballard et al., Chem. Abs., 1967, vol. 67, p. 6907z.
Nurmukhametov et al., Chem. Abs., 1966, vol. 65, p. 6533.
Ludwig et al., Zeitschrift fur Naturforschung (1961), vol. 166, pp. 638–644. (C.A. 1962, p. 218).

Primary Examiner—Dale R. Ore
Attorney, Agent, or Firm—Dennis P. Clarke

[57] ABSTRACT

A suntan composition adapted for application to the human skin which protects against burning and promotes tanning comprising a carrier having distributed therein a fluorescent compound which is non-toxic to the human skin and which absorbs ultraviolet radiation of wave lengths erythemal to the human skin below about 3150 A and converts the absorbed radiation into fluorescent emission having wavelengths which non-erythemally tan the human skin in the range of 3150 to 4000 A.

9 Claims, No Drawings

SUNTAN COMPOSITION CONTAINING FLUORESCENT COMPOUNDS

BACKGROUND OF THE INVENTION

There are many known compositions for application to the human skin to protect it from the burning radiation of natural sunlight. Much research has taken place to determine the components of sunlight radiation which produce the phenomenon known as "sunburn" or erythema. Although there is some disagreement regarding the exact limits of the range of ultra-violet wavelengths which produce erythema, it has generally been established that wavelengths below about 3150 A, particularly in the range of from about 2900 A to about 3150 A produce the erythema. The peak erythema producing wavelength may vary, depending upon the individual exposed; however, for most humans the peak is about 2967 A. It has also been discovered that the ultra-violet component of sunlight causes the human skin to tan. Although tanning is not fully understood, it is believed to be the result of the formation of melanin, a skin pigment and a migration of this melanin to the surface of the skin and the oxidative darkening thereof. It has been suggested that tanning is nature's method of protecting against the erythema producing regions of the sunlight radiation since the obtention of a good tan prevents erythema or burning of the skin without the necessity of resorting to suntan or sun-screen agents.

It is also believed by many people that tanning produces a healthy physiological effect on the human skin. There are also psychological benefits to be derived from a so-called "healthy tan" which is looked upon as a status symbol in many parts of the world.

Many suntan or sun-screen agents have been proposed in the past to protect the human skin from the erythema producing effects of sunlight. Unfortunately, the burning radiation, namely, that having a wavelength of from about 2900 to about 3150 A also contains much of the primary tanning radiation. Accordingly, the sun-screen agents proposed to date screen out the primary tanning as well as the burning radiation rendering it a time-consuming process for obtaining a good tan.

For many years it was thought that tanning was produced only by the same range of wavelengths that produced erythema. Recently, however, tanning has been shown to be produced by longer wavelengths ranging in some cases as high as about 6000 A.

It has recently been shown that radiation of longer wavelengths than about 3150 A produces tanning without erythema. There is not a general agreement as to the exact range of this secondary tanning radiation since there is considerable variation in the tanning sensitivities of various individuals and considerable variation in the effectiveness of different wavelengths for tanning various individuals. For average skin, however, it appears that tanning without erythema is produced in a range of from about 3150 to 4000 A with a broad peak at about 3600 A. Ultra-violet radiation at these wavelengths produces the maximum amount of tanning which can be obtained without the concurrent production of erythema. As noted above, however, this is a secondary or incidental tanning range of far less intensity than that of the lower wavelengths. Its advantage lies in the fact that tanning is produced, albeit slowly, without erythema or burning.

Included among the sun-screening agents suggested to date are benzyl salicylate, menthyl salicylate, glyceryl monosalicylate, umbelliferone acetic acid, quinine oleate, the various esters of p-amino benzoic acid, derivatives of beta-resorcylic acid, derivatives of cinnamic acid, derivatives of benzophenone, etc.

It is important to note the distinction between the "sunscreen" and "suntan" preparations which have been previously proposed to protect the skin from erythema and promote tanning. An ideal "sunscreening" agent would be opaque to all erythemal and tanning radiation, while an ideal "suntanning" agent would be opaque only to the erythemal radiation (or a controlled amount thereof) and would pass all of the nonerythemal or tanning radiation. Conventional "sun-tanning" agents pass about 10–20% of incident erythemal radiation and more than 90% of the longer wavelength tanning radiation. The "sun-screen" agents attempt to screen out more than 90% of the incident erythemal radiation and most of longer tanning wavelengths as well.

It is an object of the present invention to provide a sun-screening agent and composition which goes one step further than those of the prior art and, (1) screens out the erythema producing ultra-violet radiation of natural sunlight, (2) permits the incident tanning radiation having wavelengths above the erythema producing radiation to pass through and (3) enhances the tanning of the human skin to which it is applied by making available thereto more tanning radiation than those sun-screens heretofore available.

BRIEF DESCRIPTION OF THE INVENTION

The invention comprises a composition adapted for application to human skin which provides substantial protection against erythemal radiation and promotes non-erythemal tanning comprising an atoxic carrier suitable for application to the human skin having distributed therein a fluorescent compound which is non-toxic to the human skin and which strongly absorbs the ultra-violet radiation of wavelengths erythemal to the human skin below about 3150 A and which converts said absorbed radiation into fluorescent emission having wavelengths which non-erythemally tan the human skin in the range of between about 3150 A and about 4000 A.

The invention is predicated on the discovery of various sun-screening agents which not only screen out the erythemal portion of the ultra-violet radiation contained in sunlight while permitting the longer wavelength incident tanning radiation to pass through, but also, converts the shorter, erythemal or burning radiation into the longer wavelength radiation which promotes secondary tanning. Thus, the tanning is synergistically promoted due to the fact that the incident or secondary tanning radiation which is not blocked by the sun-screening agent is supplemented by the additional longer wavelength tanning radiation converted from the shorter erythemal burning radiation by the florescent compound included in the composition. It will be obvious that the utilization of the composition of the invention will enable one to obtain a healthy tan significantly faster than with the compositions heretofore available since it enables the exposure of the skin to more tanning radiation than heretofore possible while protecting the skin from erythema.

DETAILED DESCRIPTION OF THE INVENTION

There are many fluorescent compounds possessing the ability to absorb ultra-violet radiation in the range from about 2900 to about 3150 A and convert and reemit it efficiently as secondary tanning radiation in the range from about 3150 A to about 4000 A. These compounds are not all related structurally or with respect to other chemical and physical properties; hence, it is impossible to formulate a definition by way of conventional chemical nomenclature or structural formula which will define all of these types of compounds. Obviously, however, it would be a simple matter for one skilled in the art to submit any compound to spectrographic analysis or similar tests to obtain its radiation absorbing and fluorescent properties, molar extinction coefficient and stability for the purpose of ascertaining compounds suitable for the present invention. It is to be understood that any non-toxic fluorescent or phosphorescent compound capable of absorbing erythemal, ultra-violet radiation in the range of from about 2900 A to about 3150 A and converting or fluorescing said absorbed radiation into fluorescent emission having wavelengths non-erythemal to but having a tanning effect upon the human skin in the range of between about 3150 A to about 4000 A are suitable for inclusion in the compositions of the present invention.

It is to be understood that the fluorescent compound may be one which converts from 50–100%, preferably more than about 75% of the erythemal radiation into the longer wavelengths secondary tanning radiation, it being understood that these percentage figures cover the range of the products of quantum efficiencies times the radiation spectra of the proposed compounds.

Three generalizations are possible, however, in that most of the fluorescent compounds suitable for use in the sun-screening composition of the invention are either p-oligophenylenes, substituted indoles or stilbenes.

Suitable fluorescent compounds include 4-vinylbiphenyl, or those represented by one of the following structural formulae:

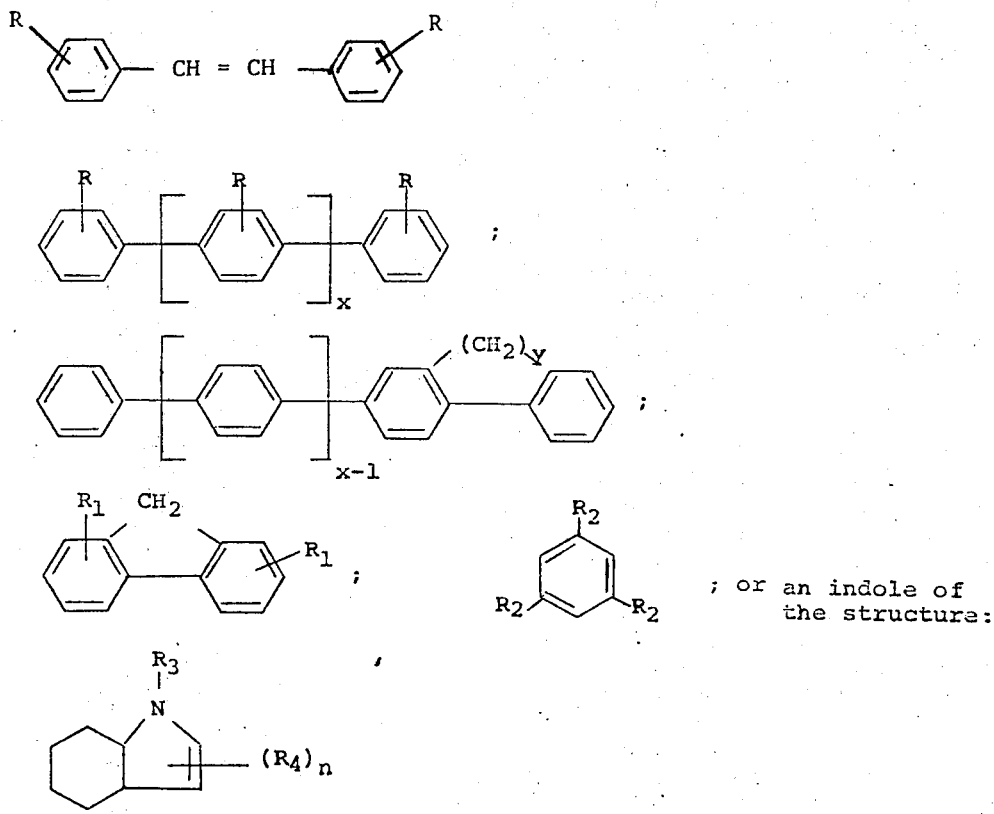

wherein:
R may be hydrogen, lower alkyl or lower alkoxy;
$x$ is an integer from 1 to about 6;
$y$ is 1 or 2;
$R_1$ is hydrogen or lower alkyl;
$R_2$ is hydrogen or a diphenylyl radical, provided that at least 2 $R_2$ groups are diphenylyl radicals;
$R_3$ is hydrogen, lower alkyl, phenyl or diphenylyl;
$R_4$ is lower alkyl or phenyl, and
$n$ is 1 or 2.

Specific compounds suitable for use in the suntan composition of the invention include, in addition to those specified above, 2-phenyl indole; 1-methyl-2-phenyl indole; 1-neopentyl-2-phenyl indole; 1,2-diphenyl indole; 1-diphenylyl-2-phenyl indole and 1,3-dimethyl-2-phenyl indole. The stilbene compounds used are preferably the trans isomers.

The most preferred fluorescent compound, however, is p-terphenyl. It has been found that this compound combines excellent properties of radiation absorption and refluorescence and applicability to the human skin for sun-screening and tanning promotion effects.

Generally, the amount of fluorescent compound included in the suntanning composition depends both upon the absorption characteristics of the compound and upon the carrier employed since the carrier dictates the amount of fluorescent compound which ultimately becomes spread upon the skin. Obviously, the protection and tanning promotion effects depend upon the maintenance of a continuous film of the fluorescent compound on the skin. The efficiency of the carrier material employed to apply the fluorescent compound to the skin will affect the required concentration of the compound in the composition. Generally, however, amounts in the range of from about 1 to about 25 percent by weight of the fluorescent compound, based upon the weight of the carrier composition employed are suitable. A more preferred range is from about 1.5 to about 15 percent by weight, again, based upon the weight of the carrier material employed. A figure corresponding to the approximate optimum concentration (wt. %) may be calculated for each compound as the product of 200 times the ratio of the molecular weight of the fluorescent compound to its molar extinction coefficient at 3100 A. It is emphasized that this value will only approximate the optimum concentration inasmuch as there are many variables which must be taken into account such as whether the compound is a liquid or a solid, etc.

The composition of the invention is applied to the human skin in an amount such that (even after evaporation, if any, of the carrier) no more than 20% of the 3000 A to 3150 A radiation is transmitted to the skin. Obviously, this amount will vary depending upon the particular fluorescent compound employed. However, for most fluorescent compounds, the amount uniformly distributed on a square centimeter of skin may vary from about $0.2M/\epsilon$ to about $5M/\epsilon$ mg., preferably from about $0.3M/\epsilon$ to $2M/\epsilon$ mg wherein M is the molecular weight of the fluorescent compound and $\epsilon$ is its molar extinction coefficient.

The particular carrier material employed in the composition in the invention is not critical. It is very desirable only that the carrier be or contain a solvent for the fluorescent compound, or that it be a film former, suitable for application to and non-toxic to the human skin. It is also necessary, of course, that the carrier be inert with respect to the fluorescent sun-screening compound.

Generally, any atoxic cosmetic composition which is substantially permeable to the absorbed and emitted ultraviolet radiation can be considered for use in the composition of the invention. Such cosmetic carriers include creams, lotions, powders, oils, volatile solvents, etc. Such cosmetic carriers are well known and conventional in the prior art and an exhaustive list thereof is unnecessary. Included among the carriers which may be employed are aqueous lower alkanol (ethanol) solutions, oils such as sesame oil, soy bean oil, safflower oil, acetylated lanolin alcohols, lanolin, polyoxyethylene sorbitan esters. Also suitable are such film formers as methyl Cellosolve, butyl Cellosolve, glycerin, castor oil, lauryl alcohols, glyceryl ricinoleates, silicones, etc. Atoxic animal, mineral or vegetable oil may be employed. To form suitable lotions, creams, etc., various well known emulsifying agents may be incorporated therein to provide the proper viscosity.

It is also possible to admix the fluorescent compound with a powder such as talc, baby powder, etc. However, the utilization of particulate sun-screening agents presents the problem that a discontinuous film of the sun-screening agent is applied to the surface of the skin, thereby affording somewhat less effective protection.

Many of the fluorescent compounds are soluble in the various solvents and/or oils listed above. Where the fluorescent compound is insoluble in the particular carrier selected, it may be suspended or emulsified therein employing well-known emulsifying agents well known in the cosmetic arts.

It is sufficient that the carrier employed be one which when applied to the human skin either forms a film thereon containing the fluorescent compound suspended or dissolved therein to provide a continuous screen of the fluorescent compound to afford optimum protection against burning and tanning enhancement; or be one which when it evaporates leaves a film of the fluorescent compound on the skin.

It is a further feature of the invention that the fluorescent compound may be coated with or dissolved in an inert atoxic medium which is permeable to both the absorbed and emitted ultra-violet radiation. Thus, the fluorescent compound may be micro-encapsulated according to known processes by such film formers as gelatin, polyvinyl alcohol, ethylcellulose, polyvinyl chloride, etc. The fluorescent compound may be micro-encapsulated by intimately admixing the fluorescent compound and, for example, gelatin in water and then adding a material such as gum arabic which operates to concentrate the gelatin or polymer into tiny liquid droplets. These droplets then coacervate to form a film or coating around the particle of the fluorescent compound as a consequence of the low interfacial tensions of the polymer. The residual water is removed leaving the encapsulated product. Obviously, many microencapsulation processes may be employed to produce the encapsulated product. Microencapsulation would enable the utilization in the composition of the invention, fluorescent compounds which would otherwise be toxic to the human skin. The compound need be merely micro-encapsulated in a material which will not permit contact with the skin but which will be permeable to the absorbed radiation and refluoresced tanning radiation.

In addition, the suntaning agents may be incorporated in aerosol sprays.

The absorption and emission data for several compounds which may be employed in the sun-screening composition of the invention are set forth in the following table. In the table $\epsilon$ represents the molar extinction coefficient at the indicated wavelength. Fluor C. G. is the center of gravity of the fluorescent emission. Qeff. is the quantum efficiency of fluorescence in cyclohexane as a solvent.

Table 1

| cpd | $\epsilon 3100 \times 10^3$ | Fluor C.G. | Qeff. |
| --- | --- | --- | --- |
| p-terphenyl | 4 | 3418 | 0.93 |
| p-quaterphenyl | 28 | 3650 | 0.9 |
| Fluorene | | 3134 | 0.80 |
| 4-methyl p-terphenyl | 6 | 3460 | 0.94 |
| 3,3''-dimethyl-p-terphenyl | 6 | 3500 | 0.9 |
| 4-(3,3-dimethyl butoxy) p-terphenyl | 17 | 3600 | 0.89 |
| 2,2' methylene-p-terphenyl | 25 | 3400 | 0.91 |
| 2,2'' ethylene-p-terphenyl | 22 | 3500 | 0.84 |
| 3,3'''-dimethyl-p-quaterphenyl | 32 | 3700 | 1.0 |

Table 1-continued

| cpd | ε3100 ×10³ | Fluor C.G. | Qeff. |
|---|---|---|---|
| 2-phenyl indole | 27 | 3730 | 0.86 |
| 1-methyl-2-phenyl indole | 15 | 3790 | 0.85 |
| 1-neopentyl -2-phenyl indole | 12 | 3760 | 0.80 |
| 1,2 diphenyl indole | 18 | 3690 | 0.90 |
| 1-(4-biphenyl)-2-phenyl indole | 25 | 3700 | 0.83 |
| 2-phenyl-3,2'-trimethylene indole | 25 | 3810 | 0.76 |
| 1¹,4⁴-di(2-butyloctyloxy)-p-quaterphenyl | 54 | 3850 | 0.93 |
| 1,3-dimethyl-2-phenyl indole | 12 | 3800 | 0.73 |
| 4-vinyl biphenyl | 3 | 3300 | 0.61 |
| diethyl-p-quinquiphenyl | 40 | 3700 | 0.92 |
| tetramethyl-p-hexaphenyl | 40 | 3700 | 0.94 |
| di(3-ethylheptyl)-p-quinquiphenyl | 62 | 3800 | 1 |
| Trans-stilbene | 24 | 3800 | 0.95 |
| 4 methyl-trans-stilbene | 32 | ~3800 | ~0.9 |
| 4,4' dimethyl-trans-stilbene | 32 | ~3800 | ~0.9 |
| 2-methyl-trans-stilbene | 32 | ~3800 | ~0.9 |

Samples of suntan compositions according to the invention were prepared according to the following nonlimiting examples. It is to be understood that conventional preservatives, odorants and additives can be included in the basic preparations set forth below without affecting the function thereof.

1. Suntan Cream

| | Weight % |
|---|---|
| Hydrophilic Ointment USP XIV | 50.00 |
| Anhydrous lanolin USP | 47.50 |
| Filter (p-quaterphenyl) - finely ground | 2.50 |

The ingredients were mixed thoroughly with a spatula on a plate until a cream-like consistency was attained.

2. Suntan Cream

| | Weight % |
|---|---|
| HEB cream base - hydrophilic ointment (Barnes Hind, Sunnyvale, Calif.) comprising methyl paraben, propyl paraben, sodium lauryl sulfate, propylene glycol, stearyl alcohol, white petrolatum, cetyl alcohol and water | 42.50 |
| Anhydrous lanolin USP | 42.50 |
| Filter (p-terphenyl) - finely ground | 15.00 |

The ingredients were mixed thoroughly with a spatula on a plate until a creamlike consistency was attained.

3. Suntan Gel

| | Weight % |
|---|---|
| A) Stearic acid | 8.50 |
| Ethyl alcohol | 49.00 |
| Filter (2-phenylindole) | 2.10 |
| B) Sodium hydroxide | 1.35 |
| ethyl alcohol | 39.05 |

A) and B) were warmed to 60° in separate containers, and stirred until dissolved. Then B) and A) were poured together to form gel.

4. Suntan Gel

| | Weight % |
|---|---|
| A) Stearic acid | 8.20 |
| Methyl alcohol | 28.00 |
| B) Sodium hydroxide | 1.30 |
| Ethyl alcohol | 50.00 |
| C) Filter (p-quaterphenyl) | 2.50 |
| Silicone (Dow-Corning 200 silicone oil, viscosity 100 cs) | 10.00 |

Filter was mixed thoroughly with silicone oil using spatula on plate; and taking care that filter was finely powdered and dispersed in silicone. A) and B) were warmed to 60° C in separate containers and were stirred until the solids dissolved. C) was then added to A) with strong stirring. B) was next added to form gel.

5. Suntan Aerosol Spray

| | Weight % |
|---|---|
| A) Anhydrous lanolin | 5.00 |
| Silicone oil (Dow-Corning 200 silicone oil, viscosity 100 cs) | 5.00 |
| Filter (p-quaterphenyl) | 2.50 |
| B) Sodium Alginate (Kelgin RL - 1 % aqueous solution - Kelco Co.) | 1.00 |
| C) Freon 11 | 86.50 |

To make concentrate: Ingredients of A) were mixed by spatula on a flat plate, taking care that filter was finely powdered and uniformly dispersed in the lanolin-oil salve. B) was next added while continuing to mix in the same fashion. C) was then added with stirring.

Aerosol formulation

| | Weight % |
|---|---|
| Concentrate | 75 |
| Freon 12 | 25 |

The concentrate and Freon are intimately admixed and stored in an air-tight conventional aerosol dispenser.

6. Suntan Aerosol Spray

| | Weight % |
|---|---|
| A) Alcohol, anhydrous ethyl | 46.00 |
| Filter (2-phenylindole) | 2.00 |
| Silicone oil (Dow-Corning 200 silicone oil, viscosity 100 cs) | 5.00 |
| B) Freon 11 | 47.00 |

To make concentrate: The ingredients of A) were heated to 50° C and stirred until the filter completely dissolved. B) was added after A) had cooled to room temperature.

Aerosol formulation

| | Weight % |
|---|---|
| Concentrate | 66.67 |
| Freon 12 | 33.33 |

The concentrate and freon were intimately admixed and stored in a conventional aerosol dispenser.

7. Suntan lotion

| | Weight % |
|---|---|
| A) Ethyl alcohol | 66.00 |
| Filter (2-phenylindole) | 1.00 |
| B) Glycerin | 10.00 |
| Water | 23.00 |

Filter was dissolved in alcohol at 50° C. Glycerin and water were added to the solution, stirred and allowed to cool.

8. Suntan lotion

| | Weight % |
|---|---|
| Ethyl alcohol | 98.00 |
| Filter (2-phenyl indole) | 2.00 |

Filter was dissolved in alcohol.

The above samples were spread on the underside of a human forearm in a grid pattern. Certain grid spaces were left untreated as controls. One full set of test areas was exposed to a GE type RS sunlamp (emission spectrum similar to sunlight in ultraviolet region below 3200 A) at a 16 inch distance for 5 minutes. A second full set of test areas was exposed to the same lamp at the same distance for 10 minutes. Similar exposures were made for 15 and 25 minutes. The areas were examined for erythema 10 hours after exposure.

The results of the test are summarized in Table 2. The examples set forth in the Table correspond to those set forth above.

Table 2

| Example | Degree of erythema | | | | | Comments |
|---|---|---|---|---|---|---|
| | None (white) | light | medium (pink) | strong (red) | severe (very red) | |
| 5 | 15 | 25 | | | | p-quaterphenyl gel |
| 1 | | | 15 | 25 | | p-quaterphenyl ointment |
| 2 | | | 15 | 25 | | p-terphenyl ointment |
| 3 | 15 | 25 | | | | 2-phenyl indole gel |
| Control | | | 10 | | 15 | no filter |
| 7 | 25 | | | | | 2-phenyl indole spray |
| 8 | | | 15 | 25 | | 2-phenyl indole lotion |
| 9 | 15 | | | 25 | | 2-phenyl indole in alcohol |
| Control | | | 10 | | 15 | no filter |
| 6 | | | 15 | 25 | | p-quaterphenyl spray |
| Control | | | 10 | | 15 | no filter |

The numbers indicate the exposure time for a given redness. Thus p-quaterphenyl gel gave no erythema from 15 minutes exposure and barely discernible erythema from 25 minute exposure, when examined ten hours later.

All areas treated with the compositions of the invention showed a medium, healthy tan following exposure, whereas the control areas were pink 24 hours following exposure.

I claim:

1. A composition adapted for application to the human skin which provides substantial protection against erythemal radiation and promotes non-erythemal tanning which consists essentially of an inert, cosmetic carrier suitable for application to the human skin having distributed therein from about 1 to about 25% by weight of a fluorescent compound which is non-toxic to the human skin and which absorbs ultra-violet radiation of wavelengths erythemal to the human skin between about 2900 A and about 3150 A and which converts said absorbed radiation into fluorescent emission having wavelengths which non-erythemally tan the human skin in the range of between about 3150 A and about 4000 A, said fluorescent compound having one of the structural formulae:

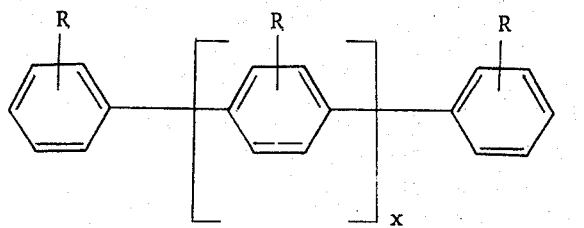

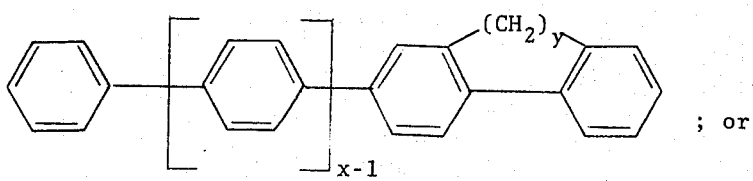

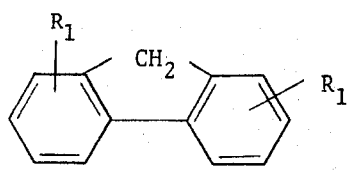

wherein

R is hydrogen, lower alkyl or lower alkoxy;
$x$ is an integer from 1 to 6;
$y$ is 1 or 2; and,
$R_1$ is hydrogen or lower alkyl.

2. The composition of claim 1 wherein said fluorescent compound is p-terphenyl.

3. The composition of claim 1 wherein said fluorescent compound is coated with or dissolved in an inert, atoxic medium which is permeable to both the absorbed and emitted ultra-violet radiation.

4. The composition of claim 1 wherein said carrier is a cosmetic composition which is substantially permeable to said absorbed and emitted ultra-violet radiation.

5. The composition of claim 1 wherein said carrier is a cream.

6. The composition of claim 1 wherein said carrier is a lotion.

7. The composition of claim 1 wherein said fluorescent compound is dissolved in said carrier.

8. The composition of claim 1 wherein said fluorescent compound is suspended in said carrier.

9. The composition of claim 1 wherein said fluorescent compound is microencapsulated in a material which will not permit contact of the fluorescent compound with the skin but which is permeable to the absorbed radiation and the re-fluoresced radiation.

* * * * *